(12) United States Patent
Chen et al.

(10) Patent No.: US 9,376,641 B2
(45) Date of Patent: Jun. 28, 2016

(54) METAL-ORGANIC FRAMEWORK WITH OPTIMIZED OPEN METAL SITES AND PORE SPACES FOR HIGH METHANE STORAGE AT ROOM TEMPERATURE

(75) Inventors: Banglin Chen, San Antonio, TX (US); Zhiyong Guo, San Antonio, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/984,724

(22) PCT Filed: Feb. 15, 2012

(86) PCT No.: PCT/US2012/025206
§ 371 (c)(1),
(2), (4) Date: Mar. 6, 2014

(87) PCT Pub. No.: WO2012/112660
PCT Pub. Date: Aug. 23, 2012

(65) Prior Publication Data
US 2014/0194639 A1 Jul. 10, 2014

Related U.S. Application Data

(60) Provisional application No. 61/443,065, filed on Feb. 15, 2011.

(51) Int. Cl.
| | |
|---|---|
| C07F 1/08 | (2006.01) |
| C10L 3/00 | (2006.01) |
| B01J 20/22 | (2006.01) |
| C07C 63/331 | (2006.01) |
| F17C 11/00 | (2006.01) |
| C10L 3/10 | (2006.01) |

(52) U.S. Cl.
CPC .............. *C10L 3/003* (2013.01); *B01J 20/226* (2013.01); *C07C 63/331* (2013.01); *C07F 1/08* (2013.01); *C10L 3/10* (2013.01); *F17C 11/005* (2013.01)

(58) Field of Classification Search
USPC ......................................... 556/110, 115, 112
See application file for complete search history.

(56) References Cited

U.S. PATENT DOCUMENTS

| | | | |
|---|---|---|---|
| 2003/0004363 A1 | 1/2003 | Koncar et al. | |
| 2006/0252641 A1* | 11/2006 | Yaghi et al. | 502/401 |
| 2010/0069234 A1 | 3/2010 | Willis et al. | |

OTHER PUBLICATIONS

Zhenxia; Crystal Growth and design, vol. 10, No. 6, p. 2775-2779; published on Apr. 30, 2010.*
Yan et al. "Exceptionally High H2 Storage by a Metal-organic Polyhedral Framework" The Royal Society of Chemistry, Jan. 2009, pp. 1025-1027.
Schnobrich et al. "Linker-Directed Vertex Desymmetrization for the Production of Coordination Polymers with High Porosity", JACS Articles, Sep. 14, 2010, pp. 13941-13948.
European Search Report from Application No. 12747419.5-1451, dated Jun. 25, 2014, pp. 1-7.
PCT Search Report from Application No. PCT/US2012/025206, dated Dec. 12, 2012, pp. 1-4.
Barone et al. "Role and Effective Treatment of Dispersive Forces in Materials: Polyethylene and Graphite Crystals as Test Cases" J. Comput. Chem. 2009, 30, 934.
Burchell et al. "Low Pressure Storage of Natural Gas for Vehicular Applications" SAE Tech. Pap. Ser. 2000, 2000-01-2205.
Chen et al. "A New Multidentate Hexacarboxylic Acid for the Construction of Porous Metal-Organic Frameworks of Diverse Structures and Porosities" Crystal Growth & Design, 2010, 10, 2775.
Chen et al. "Metal-Organic Frameworks with Functional Pores for Recognition of Small Molecules" Acc. Chem. Res. 2010, 43, 1115.
Czaja et al. "Industrial applications of metal-organic frameworks" Chem. Soc. Rev. 2009, 38, 1284.
Dinca et el. "Hydrogen Storage in Microporous Metal-Organic Frameworks with Exposed Metal Sites" Angew. Chem. Int. Ed. 2008, 47, 6766.
Dueren et al. "Calculating Geometric Surface Areas as a Characterization Tool for Metal-Organic Frameworks" J. Phys. Chem. C, 2007, 111, 15350.
Dueren et al. "Using molecular simulation to characterise metal-organic frameworks for adsorption applications" Chem. Soc. Rev. 2009, 38, 1237.
Eddaoudi et al. "Systematic Design of Pore Size and Functionality in Isoreticular MOFs and Their Application in Methane Storage" Science, 2002, 295, 469.
Farha et al. "De novo synthesis of a metal-organic framework material featuring ultrahigh surface area and gas storage capacities" Nat. Chem. 2010, 944.
Fàrey et al. "Large breathing effects in three-dimensional porous hybrid matter: facts, analyses, rules and consequences" Chem. Soc. Rev. 2009, 38, 1380.
Giannozzi et al. "Quantum Espresso: a modular and open-source software project for quantum simulations of materials" J. Phys.: Condens. Matter 2009, 21, 395502.
Kim et al. "Methane Sorption and Structural Characterization of the Sorption Sites in Zn2(bdc)2(dabco) by Single Crystal X-ray Crystallography" Chem. Asian J. 2009, 4, 886.

(Continued)

*Primary Examiner* — Pancham Bakshi
(74) *Attorney, Agent, or Firm* — Meyertons, Hood, Kivlin, Kowert & Goetzel, P.C.; Eric B. Meyertons

(57) ABSTRACT

A 3D porous metal-organic framework and method of making are described. In some embodiments, a 3D porous metal-organic framework may be based on a trinodal (3,3,4) net of zyg topology by the self-assembly of the nonlinear hexacarboxylate (BHB) with the paddle-wheel $Cu_2(COO)_4$ cluster. Although its porosity and surface area are moderate, the open copper sites and optimal pore spaces enable the pore spaces to be fully utilized for methane storage, resulting in a high methane storage density and high absolute volumetric methane storage at room temperature and 35 bar. By the immobilization of high density open metal sites and the deliberate control of the pore space for their efficient methane storage, this porous MOF functions as an efficient media for methane and natural gas storage.

5 Claims, 4 Drawing Sheets

(56) References Cited

OTHER PUBLICATIONS

Kondo et al. "Microporous Materials Constructed from the Interpenetrated Coordination Networks. Structures and Methane Adsorption Properties" Chem. Mater. 2000, 12, 1288.

Lan et al. "A Luminescent Microporous Metal-Organic Framework for the Fast and Reversible Detection of High Explosives" Angew. Chem. Int. Ed., 2009, 48, 2334.

Llewellyn et al. "High Uptakes of $CO_2$ and $CH_4$ in Mesoporous Metal-Organic Frameworks MIL-100 and MIL-10" Langmuir 2008, 24, 7245.

Ma et al. "Enantioselective catalysis with homochiral metal-organic frameworks" Chem. Soc. Rev. 2009, 38, 1248.

Ma et al. "Metal-Organic Framework from an Anthracene Derivative Containing Nanoscopic Cages Exhibiting High Methane Uptake" J. Am. Chem. Soc. 2008, 130, 1012.

Millward et al. "Metal-Organic Frameworks with Exceptionally High Capacity for Storage of Carbon Dioxide at Room Temperature" J. Am. Chem. Soc., 2005, 127, 17998.

Morris et al. "Gas Storage in Nanoporous Materials" Angew. Chem. Int. Ed. 2008, 47, 4966.

Noro et al. "A New, Methane Adsorbent, Porous Coordination Polymer [{$CuSiF_6$(4,4'-bipyridine)2}n]" Angew. Chem. Int. Ed. 2000, 39, 2081.

Nouar et al. "Supermolecular Building Blocks (SBBs) for the Design and Synthesis of Highly Porous Metal-Organic Frameworks" J. Am. Chem. Soc.2008, 130, 1833.

O'Keeffe et al. "The Reticular Chemistry Structure Resource (RCSR) Database of, and Symbols for, Crystal Nets" Accounts Chem. Res. 2008, 41, 1782.

Thomas "How Far is the Concept of Isolated Active Sites Valid in Solid Catalysts?" Topics in Catalysis, 2008, 50, 98.

Wang et al. "Metal-Organic Frameworks Based on Double-Bond-Coupled Di-Isophthalate Linkers with High Hydrogen and Methane Uptakes" Chem. Mater. 2008, 20, 3145.

Wu et al. "High-Capacity Methane Storage in Metal-Organic Frameworks M2(dhtp): The Important Role of Open Metal Sites" J. Phys. Chem. C 2009, 113, 3029.

Wu et al. "Metal-Organic Frameworks with Exceptionally High Methane Uptake: Where and How is Methane Stored?" Chem. Eur. J. 2010, 16, 5205.

Xiang et al. "Exceptionally High Acetylene Uptake in a Microporous Metal-Organic Framework with Open Metal Sites" J. Am. Chem. Soc., 2009, 131, 12415.

Xiang et al. "Open Metal Sites within Isostructural Metal-Organic Frameworks for Differential Recognition of Acetylene and Extraordinarily High Acetylene Storage Capacity at Room Temperature" Angew. Chem. Int. Ed., 2010, 49, 4615.

Yaghi et al. "Reticular synthesis and the design of new materials" Nature 2003, 423, 705.

Yan et al. "Metal-Organic Polyhedral Frameworks: High $H_2$ Adsorption Capacities and Neutron Powder Diffraction Studies" J. Am. Chem. Soc. 2010, 132, 4092.

Yuan et al. "An Isoreticular Series of Metal-Organic Frameworks with Dendriti Hexacarboxylate Ligands and Exceptionally High Gas-Uptake Capacity" Angew. Chem. Int. Ed. 2010, 49, 5357.

Zhang et al. "Versatile Structure-directing Roles of Deep Eutectic Solvents and Their Implication in Generation of Porosity and Open Metal Sites for Gas Storage" Angew. Chem. Int. Ed. 2009, 48, 3486.

Zhou "Methane storage in porous metal-organic frameworks: current records and future perspectives" Chem. Rec. 2010, 10, 200.

\* cited by examiner

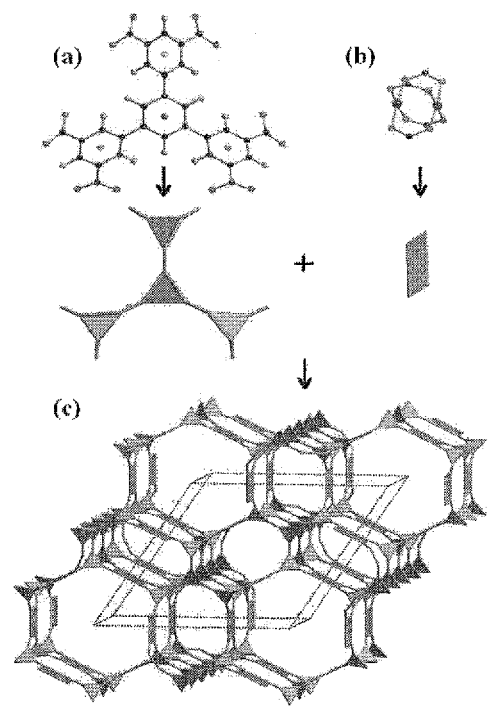
FIG. 1a-c
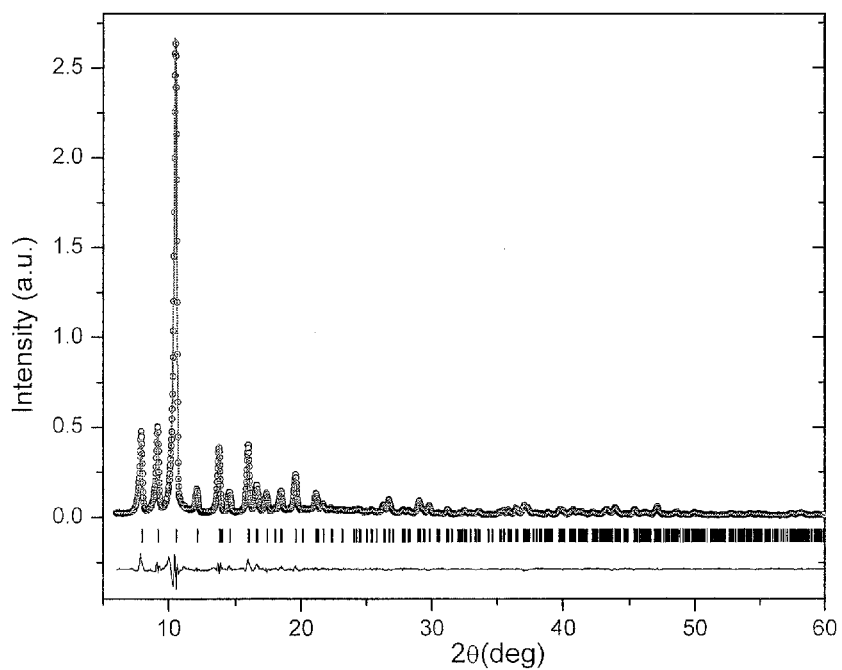
FIG. 2

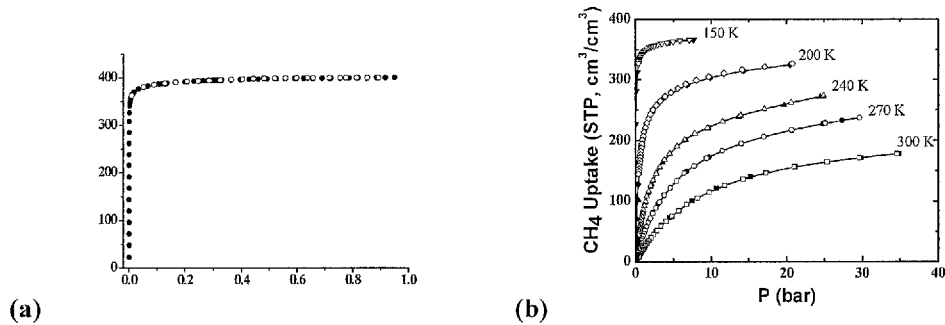
FIG. 6a-b
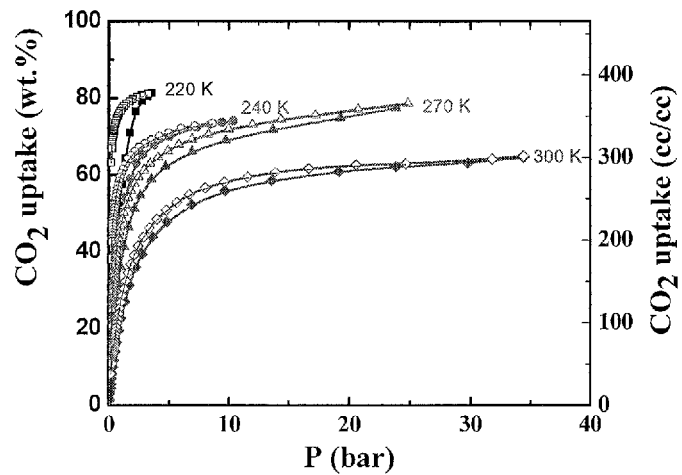
FIG. 7
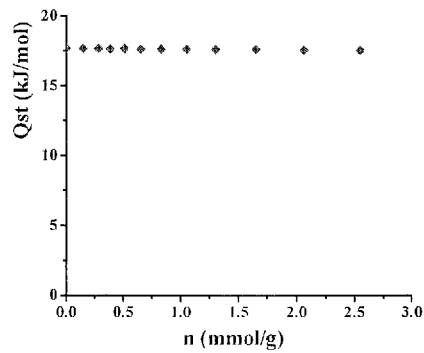
FIG. 8

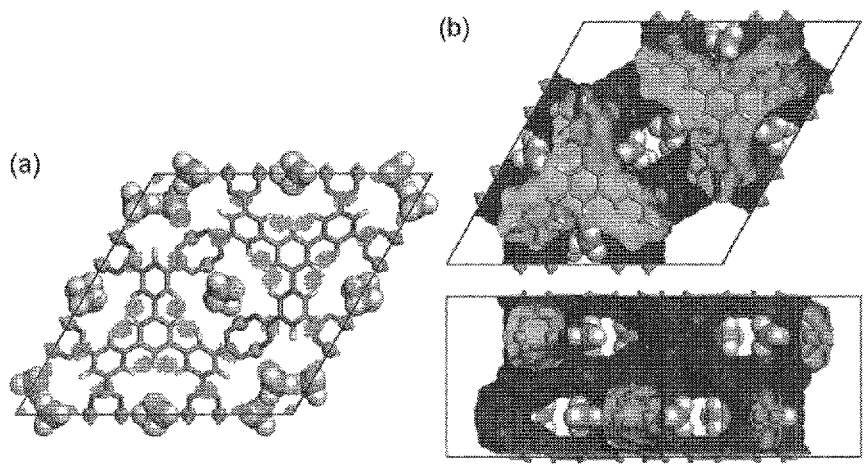
FIG. 9a-b
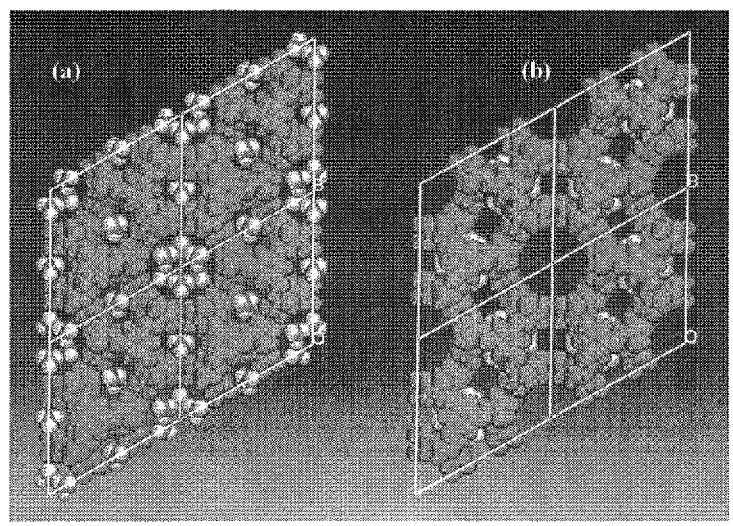
FIG. 10a-b

US 9,376,641 B2

1

METAL-ORGANIC FRAMEWORK WITH OPTIMIZED OPEN METAL SITES AND PORE SPACES FOR HIGH METHANE STORAGE AT ROOM TEMPERATURE

STATEMENT REGARDING FEDERALLY SPONSORED RESEARCH OR DEVELOPMENT

This invention was made with government support under grant no. CHE0718281 awarded by the National Science Foundation. The government has certain rights in the invention.

BACKGROUND OF THE INVENTION

1. Field of the Invention

The present disclosure generally relates to a metal-organic framework for the efficient storage of one or more gases. More particularly, the disclosure generally relates to systems and methods for formulating and synthesizing a metal-organic framework for optimized methane storage.

2. Description of the Relevant Art

Realization of high capacity gas storage materials is essential to make use of clean energy resources such as hydrogen, methane (e.g., natural gas) and acetylene in the future. Although there has been extensive research on gas storage materials, no feasible hydrogen storage material has been achieved so far that meets the storage capacity needed at room temperature and moderate pressure. The stable nature of methane, relative to acetylene, is considered to be the most promising alternative energy source especially for mobile applications.

Recently there has been interest in the use of metal-organic frameworks (MOFs) for storing gases useful for fueling various systems or devices (e.g., vehicles). Highly porous MOFs with large pore spaces and high surface areas appear to favor high gas storage capacities. However, the relatively weak interactions between the MOFs and the gas molecules have limited their high gas storage capacities only to low temperatures (for example, 77 K for $H_2$) and/or high pressure (up to 100 bar) in order to fully utilize the pore space. Furthermore, the low framework densities of some extremely porous MOFs have also limited their volumetric gas storage capacities. Framework densities are another important parameter for the practical implementation of such materials in mobile applications. In some embodiments, ideal MOF materials for high volumetric gas storage are those with moderate porosities in which the pore spaces and functional sites are efficiently utilized because of strong interactions with gas molecules; thus their storage capacities can be maximized at higher temperatures (e.g., room temperature) and lower pressure (e.g., 35 bar).

What is needed therefore is a MOF which efficiently and safely stores gases (e.g., methane, natural gas) at room temperature.

SUMMARY

Embodiments of the present invention address the problems described above by providing novel compositions and methods for storing gases at room temperature. Embodiments of the present invention provide unique methods and compositions that are safe and effective for storing gases, especially for fueling purposes.

In some embodiments, a method of storing gases in a metal-organic framework may include using a microporous framework to optimize methane storage density and volumetric methane storage. The microporous framework may include open copper sites and channel-like pore spaces.

In some embodiments, a metal-organic framework may include a 3,3',3'',5,5',5''-benzene-1,3,5-triyl-hexabenzoate or a derivative thereof and a copper. The 3,3',3'',5,5',5''-benzene-1,3,5-triyl-hexabenzoate or derivative thereof and the copper may coordinate to one anther to form a microporous framework comprising open copper sites and channel-like pore spaces.

In some embodiments, a metal-organic framework may be prepared by a process including reacting 3,3',3'',5,5',5''-benzene-1,3,5-triyl-hexabenzoic acid and a copper salt and an acid in a polar solvent. The process may include allowing the reaction to run at an elevated temperature for at least one day. The process may include separating the metal-organic framework from the polar solvent.

In some embodiments, a method of making a metal-organic framework may include reacting 3,3',3'',5,5',5''-benzene-1,3,5-triyl-hexabenzoic acid and a copper salt and an acid in a polar solvent. The method may include allowing the reaction to run at an elevated temperature for at least one day. The method may include separating the metal-organic framework from the polar solvent.

In some embodiments, the polar solvent may include N,N-dimethylformamide. In some embodiments, the copper salt may include $Cu(NO_3)_2$. In some embodiments, the copper salt comprises $Cu(NO_3)_2 \cdot 2.5H_2O$. In some embodiments, the elevated temperature is at least about 50° C. In some embodiments, the reaction is allowed to run at an elevated temperature for at least two days. In some embodiments, the method and/or process includes activating the metal-organic framework by heating the metal-organic framework above 100° C. for about one day under high vacuum.

BRIEF DESCRIPTION OF THE DRAWINGS

Advantages of the present invention may become apparent to those skilled in the art with the benefit of the following detailed description of the preferred embodiments and upon reference to the accompanying drawings.

FIGS. 1a-c depict the building units of an embodiment of UTSA-20. (a-b) The secondary building units (SBUs) of UTSA-20 (C, black; O, red; Cu blue). The isolated blue and green points on the BHB linker indicate the branching points (nodes) of the underlying zyg net. Middle, the SBUs abstracted as geometric shapes. (c) The assembly of these shapes in UTSA-20. The topology is zyg-a—the augmented zyg net in which coordination figures (in this case squares and triangles) replace the original vertices.

FIG. 2 depicts experimental (circles), fitted (line), and difference (noisy line below observed and calculated patterns) XRD profiles for activated UTSA-20 at 298 K. Vertical bars indicate the calculated positions of Bragg peaks for UTSA-20.

FIGS. 6a-b depict (a) nitrogen sorption isotherm at 77 K and (b) variable temperature dependent high pressure excess methane sorption isotherms of UTSA-20.

FIG. 7 depicts high pressure excess carbon dioxide sorption isotherms of UTSA-20 at different temperatures.

FIG. 8 depicts coverage dependency of the adsorption enthalpies for $CH_4$ in UTSA-20 calculated from virial fits of their 200, 240, 270 and 300 K sorption isotherms.

FIGS. 9a-b depict (a) Probability distribution of the $CH_4$ center of mass in UTSA-20 ([0 0 1] view), obtained from GCMC simulation at 298 K and 10 bar. The red regions represent the places where methane molecules are heavily populated in the MOF structure. Note that the open-Cu site is preoccupied with $CH_4$ molecules in order to focus our effort on the search of other strong methane adsorption sites; (b) The pore surface of the interconnected channel pores in UTSA-20 (derived by using $N_2$ as probe molecules, based on vdW interactions), with adsorbed methane at the linker channel site (derived from DFT-D calculations). The channel width along the c-axis is in good match with the adsorbed methane molecules, leading to enhanced vdW interaction (methane molecules are shown in space-filled model for the clarity).

FIGS. 10a-b depict (a) The open copper sites and (b) linker channel sites for high density methane storage in UTSA-20.

Figure 3:
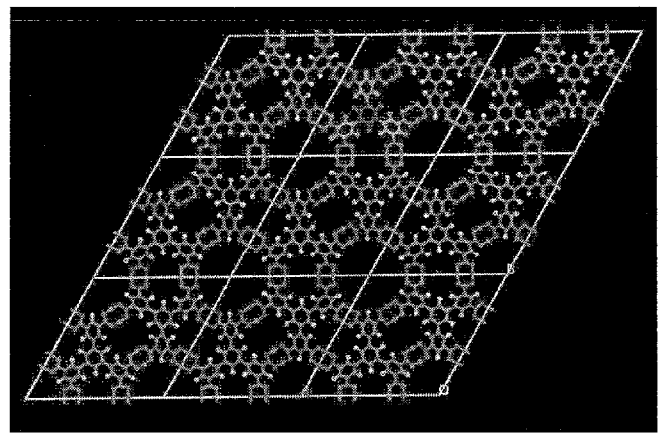
FIG. 3 depicts the crystal structure of UTSA-20 viewed along c axis (Color scheme: C, gray; H, white; O, red; Cu, orange. Both the central (blue) and peripheral (green) benzene of BHB organic linker act as the 3-coordinated triangular nodes in its trinodal (3,3,4) net of zyg topology).

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION

It is to be understood the present invention is not limited to particular devices or chemical systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

While the invention is susceptible to various modifications and alternative forms, specific embodiments thereof are shown by way of example in the figures herein and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DEFINITIONS

Unless defined otherwise, all technical and scientific terms used herein have the same meaning as commonly understood by one of ordinary skill in the art.

The phrase "linker channel site" as used herein generally refers to channel-like pore spaces between the parallel stacked linkers (e.g., BHB linkers).

The phrase "van der Waals forces" as used herein generally refers to attractions between atoms, molecules, and surfaces, as well as other intermolecular forces. Van der Waals forces typically differ from covalent and ionic bonding in that they are caused by correlations in the fluctuating polarizations of nearby particles.

Metal-Organic Frameworks

In some embodiments, a method and/or system of efficiently storing gases (e.g., methane) may include (1) immobilizing high density open metal sites and (2) constructing suitable pore spaces within a metal-organic framework. In some embodiments, a MOF capable of high density methane storage may include $Cu_3(BHB)$ ("UTSA-20"). UTSA-20 may include a structure based on the trinodal (3,3,4) net of zyg topology (FIG. 1c). UTSA-20 may be formed by the self-assembly of an organic linker (e.g., hexacarboxylate (e.g., $H_6BHB$=3,3',3",5,5',5"-benzene-1,3,5-triyl-hexabenzoic acid, FIG. 1a)) with the paddle-wheel $Cu_2(COO)_4$ SBU (FIG. 1b). In some embodiments, the organic linker may function to assist in optimizing the pore spaces. In UTSA-20 the open copper site density has been secured by the six carboxylates, while the pore spaces have been optimized by the m-benzenedicarboxylate moieties and the central benzene backbone. The high density of open copper sites and optimal pore spaces within UTSA-20 has enabled them to be fully utilized for methane storage, highlighting UTSA-20 as the material with the highest methane storage density (0.222 g/cm$^3$) in micropores at 300 K and 35 bar. The overall absolute volumetric methane storage of 195 cm$^3$/cm$^3$ has resulted in UTSA-20 being one of the very few MOFs surpassing the DOE methane storage target of 180 cm$^3$/cm$^3$ at room temperature and 35 bar.

In some embodiments, UTSA-20 may be synthesized by the solvothermal reaction of $H_6BHB$ (10 mg, 0.018 mmol) and $Cu(NO_3)_2 \cdot 2.5H_2O$ (20 mg, 0.086 mmol) in N,N-dimethylformamide (DMF) (1.5 ml) with addition of 2 drops of $HBF_4$. The reaction may be run at 65° C. for 48 hrs resulting in green small block shaped crystals (15.8 mg, 69% yield based on $H_6BHB$). The compound was formulated as $Cu_3(BHB)(H_2O)_3 \cdot (DMF)_6(H_2O)_{2.5}$ by CHN elemental microanalysis.

The acetone-exchanged UTSA-20 was activated at 120° C. for 24 hrs under high vacuum for powder X-ray diffraction and gas sorption studies. As shown in FIG. 2, the activated UTSA-20 exhibits a well resolved PXRD pattern which has allowed us to refine the structure by powder x-ray Rietveld refinement.

The in situ formed paddle-wheel $Cu_2(CO_2)_4$ SBUs are bridged by the hexadentate organic linkers BHB to construct a three-dimensional porous MOF. The MOF is based on a trinodal (3,3,4)-coordinated net of zyg topology, consisting of two kinds of 3-coordinated node, shown as blue and green triangles, and a 4-coordinated node of the paddle-wheel $Cu_2(CO_2)_4$ cluster, shown as a red square (FIG. 1). The zyg net is significantly different from the ntt one constructed from the $Cu_2(CO_2)_4$ clusters and larger hexadentate organic linkers mainly because the four benzene rings within BHB are tilted with each other and not coplanar because of the constraint of the crystal structure (FIG. 3). There exist 1D rectangular pores of about 3.4×4.8 Å and 1 D cylinders of 8.5 Å in diameter along the c axis, taking into account the van der Waals radii, with the open copper sites exposed to the pores for their potential binding and storage of gas molecules. The total accessible free volume is 3471.0 Å$^3$—63.0% of the unit volume 5512.9 Å.

Figure 4:
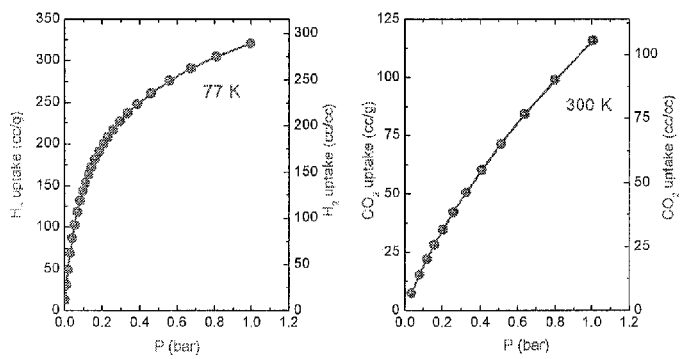
FIG. 4 depicts low pressure excess (Left) $H_2$ sorption at 77 K and (right) $CO_2$ sorption at 300 K.
Figure 5:
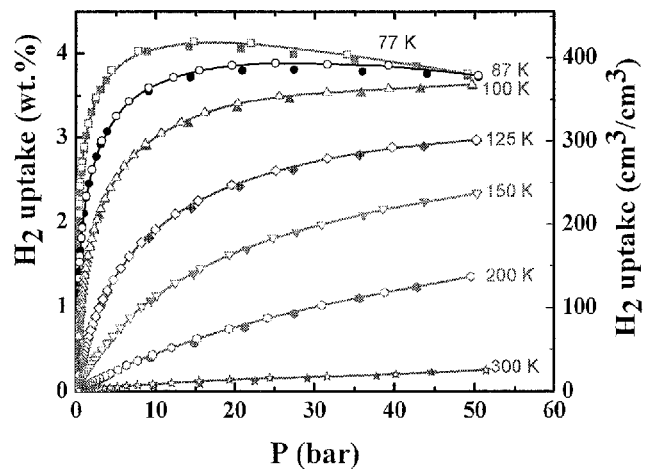
FIG. 5 depicts high pressure excess hydrogen sorption isotherms of UTSA-20 at different temperatures.

As shown in FIG. 6a, UTSA-20 exhibits type I reversible sorption isotherms and takes up $N_2$ to 402 cm$^3$/g at 77 K and 1 bar, corresponding to a BET surface area of 1156 m$^2$/g.[16] Such porosity is moderate and is even lower than those of HKUST-1 ($Cu_2(BTC)_3$, BTC=1,3,5-Benzenetricarboxylate)

and MOF-505 (Cu$_2$(BPTC), BPTC=3,3',5,5'-Biphenyltetra-carboxylate).[17] However, the high density of open copper sites and small pores are favorable to the high hydrogen storage of 2.9 wt % at 77 K and 1 bar (FIG. 4), but the moderate surface area has apparently limited its hydrogen uptake to 4.1 wt % at 77 K and 15 bar (FIG. 5). Although both N$_2$ and H$_2$ sorption isotherms indicate that UTSA-20 is of moderate porosity, it takes up significant amount of methane because of the full use of both open copper sites and optimal pore spaces for methane storage. The methane storage density at 150 K and 5 bar is 0.376 g/cm$^3$, which is 89% of that of liquid methane (0.423 g/cm$^3$). The methane storage density in micropores in UTSA-20 is 0.222 g/cm$^3$ at 300 K and 35 bar, which is almost the same as the density of compressed methane at 300 K and 340 bar, highlighting UTSA-20 as the porous material with the highest methane storage density at 300 K and 35 bar (storage density in micropores is the amount of methane stored divided by the volume of pore space). A comparison of UTSA-20 and some previously reported MOFs for their methane storage is shown in Table 1. The efficient use of the pore spaces contribute to the high excess volumetric methane storage capacity of UTSA-20 of 178 cm$^3$/cm$^3$ at 300 K and 35 bar (FIG. 6), which is slightly lower than the two best MOFs for the volumetric methane storage of about 190 cm$^3$/cm$^3$. The overall absolute volumetric methane storage capacity is 195 cm$^3$/cm$^3$ which has surpassed the DOE standard (180 cm$^3$/cm$^3$) of porous materials for methane storage at ambient temperature and 35 bar (FIG. 6b).

TABLE 1

Comparison of UTSA-20 with some previously reported MOFs for their methane storage at 298-300 K and 35 bar.

| MOFs | Surface areas (m$^2$/g) | Pore Volume (cm$^3$/g) | CH$_4$ uptake cm$^3$ (STP)/cm$^3$ | Density of adsorbed CH$_4$(g/cm$^3$)[b] |
|---|---|---|---|---|
| UTSA-20 | 1156 | 0.63 | 178 | 0.22 |
| PCN-14[21] | 1753 | 0.87 | 220[a] | 0.21 |
| Ni-MOF-74[26] | 1033 | 0.54 | 190 | 0.21 |
| IRMOF-6[20] | 2800 | 0.92 | 155 | 0.19 |
| CuSiF$_6$(4,4'-bipy)$_2$[18] | 1337 | 0.56 | 125 | 0.19 |
| PCN-11[23] | 1931 | 0.91 | 171 | 0.18 |
| Zn$_2$(bdc)$_2$-(dabco)[25] | 1450 | 0.68 | 137 | 0.17 |
| HKUST-1[27] | 1502 | 0.76 | 160 | 0.17 |
| IRMOF-1[20] | 3800 | 1.04 | 135 | 0.15 |
| MIL-101c[22] | 4230 | 2.15 | 100 | 0.08 |
| MOF-205[4] | 4460 | 2.16 | 93 | 0.08 |
| MOF-200[4] | 4530 | 3.59 | 41 | 0.04 |
| MOF-210[4] | 6240 | 3.60 | 53 | 0.04 |

[a]at 290 K;
[b]in micropores.

The open copper sites and optimal pore spaces have also enabled high excess volumetric carbon dioxide storage of UTSA-20 (301 cm$^3$/cm$^3$), which is comparable to those highly porous MOFs of much larger surfaces areas (MIL-101 (5900 m$^2$/g), 300 cm$^3$/cm$^3$; MOF-177 (5640 m$^2$/g), 323 cm$^3$/cm$^3$) (FIG. 7 and Table 2).

TABLE 2

CO$_2$ uptake in some examined metal-organic frameworks at room temperature and 35 bar.

| | Crystal Density (g/cm$^3$) | Surface areas (BET (m$^2$/g) | Pore volume (cm$^3$/g) | Excess CO$_2$ uptake (cm$^3$/cm$^3$) |
|---|---|---|---|---|
| HKUST-1 | 0.88 | 1502 | 0.76 | 211 |
| MIL-101c | 0.44 | 4230 | 2.15 | 300 |
| Ni-MOF-74 | 1.21 | 1033 | 0.54 | 263 |
| UTSA-20 | 0.91 | 1156 | 0.63 | 301 |
| IRMOF-1 | 0.61 | 3800 | 1.04 | 297 |
| IRMOF-6 | 0.65 | 2800 | 0.92 | 283 |
| MOF-177 | 0.43 | 4750 | 1.59 | 323 |
| MOF-200 | 0.22 | 4530 | 3.59 | 226 |
| MOF-205 | 0.38 | 4460 | 2.16 | 288 |
| MOF-210 | 0.25 | 6240 | 3.60 | 248 |

The coverage-dependent adsorption enthalpies of UTSA-20 to methane were calculated based on the virial method, a well established and reliable methodology from fits of their adsorption isotherms at 200, 240, 270 and 300 K. As shown in FIG. 8, UTSA-20 exhibits quite high adsorption enthalpies for CH$_4$ (17.7 kJ/mol at the zero coverage) which are slightly higher than those for other MOFs with high density methane storage.

Previous studies on methane storage in other MOFs with dicopper paddle wheel units have established that the open-Cu site binds CH$_4$ strongly and is one of the primary methane adsorption sites. It should be noted that direct binding of one methane molecule at each Cu site only accounts for a maximum storage capacity of ~89 cm$^3$(STP)/cm$^3$, half of the 178 cm$^3$(STP)/cm$^3$ as measured for UTSA-20 at RT and 35 bar. To reveal other major CH$_4$ adsorption sites, Grand Canonical Monte Carlo (GCMC) simulations of methane adsorption in UTSA-20 were performed (with the open-Cu sites preoccupied by methane) using the classical force-field method. Simulations were performed at 298 K and various pressures (0.1, 1, 10, and 35 bar). The probability distribution of adsorbed CH$_4$ was generated from the simulation after the equilibrium stage, and the result obtained at the pressure of 10 bar is shown in FIG. 3a as an example. The channel-like pore spaces between the parallel stacked BHB linkers (along the c-axis) are heavily populated by CH$_4$ molecules, and we term this site the "linker channel site". At higher pressures, additional adsorption sites may be found, but they are much weaker and less-defined adsorption sites. We note that full saturation of the open-Cu site and the linker channel site may generate a methane capacity of about 162 cm$^3$(STP)/cm$^3$, which is approximately 90% of the experimental uptake at 298 K and 35 bar. The remaining storage capacity may be provided by those additional secondary adsorption sites.

The energy aspect of adsorption of methane on the two major sites was further explored. The static methane binding energies (E$_B$) were calculated based on density-functional theory with a semiempirical correction for dispersive interactions (DFT-D). For the open-Cu site and the linker channel site, calculated E$_B$'s are 21.6 and 23.5 kJ/mol, respectively, in reasonable agreement with the above experimental Q$_{st}$ values. The methane binding at the linker channel site is even stronger than that at the open-Cu site. While the methane binding on the open-Cu site was known to be partly due to the enhanced electrostatic interaction between the metal ion and the slightly polarized methane molecule, the methane interaction with the framework at the linker channel site is mainly due to van der Waals (vdW) forces. In some embodiments, van der Waals forces account for a majority of the binding forces between the metal-organic framework and the bound gas.

In some embodiments, linker channel sites may be sized such that at least two organic linkers of a metal-organic framework interact with a guest (e.g., methane). The size of the linker channel pore was found to be just "appropriate" to enable the methane molecule interact with two BHB linkers simultaneously. To further illustrate this, in FIG. 9b, the vdW surface of the UTSA-20 channel pores was plotted along with the adsorbed methane at the linker channel sites. The methane molecule is "sandwiched" between two BHB linker potential surfaces, which results in enhanced overall interaction. The strong interactions of the both open copper sites and the linker channel sites with methane gas molecules have enabled the pore spaces within UTSA-20 to be fully utilized for methane storage, thus featuring UTSA-20 as the porous MOF with the highest methane storage densities (FIG. 10).

In some embodiments, a 3D porous metal-organic framework (e.g., UTSA-20) was realized based on a trinodal (3,3,4) net of zyg topology by the self-assembly of the nonlinear hexacarboxylate (BHB) with the paddle-wheel $Cu_2(COO)_4$ cluster. Although its porosity and surface area are moderate and much lower than most of highly porous MOFs, the open copper sites and optimal pore spaces within UTSA-20 has enabled the pore spaces to be fully utilized for methane storage. UTSA-20 has the highest methane storage density (0.222 $g/cm^3$) and is just the third porous MOF whose absolute volumetric methane storage has surpassed the DOE methane storage target of 180 $cm^3/cm^3$ at room temperature and 35 bar. By the immobilization of high density open metal sites and the deliberate control of the pore space for their efficient methane storage, these new porous MOFs are excellent media for methane and natural gas storage, particularly for mobile applications.

EXAMPLES

Having now described the invention, the same will be more readily understood through reference to the following example(s), which are provided by way of illustration, and are not intended to be limiting of the present invention.

Synthesis of UTSA-20:

UTSA-20 was synthesized by the solvothermal reaction of $H_6BHB$ (10 mg, 0.018 mmol) and $Cu(NO_3)_2 \cdot 2.5H_2O$ (20 mg, 0.086 mmol) in N,N-dimethylformamide (DMF) (1.5 ml) with addition of 2 drops of $HBF_4$ at 65° C. for 48 hrs to give green small block shaped crystals (15.8 mg, 69% yield based on $H_6BHB$). The compound was formulated as $Cu_3(BHB)(H_2O)_3 \cdot (DMF)_6(H_2O)_{2.5}$ by CHN elemental microanalysis.[15]

The acetone-exchanged UTSA-20 was activated at 120° C. for 24 hrs under high vacuum for powder X-ray diffraction and gas sorption studies. As shown in FIG. 2, the activated UTSA-20 exhibits a well resolved PXRD pattern which has allowed us to refine the structure by powder x-ray Rietveld refinement.

Powder X-Ray Crystallography:

Phase identification was conducted on samples sealed in glass capillaries, using a Rigaku X-ray diffractometer with a Cu $K_\alpha$ source. Data were collected over 14 h at room temperature in the 2θ range of 5-60° with a step size of 0.02°. The X-ray diffraction (XRD) reflections of the as-synthesized UTSA-20 samples can be indexed using a hexagonal cell with $\alpha$=21.971 Å and c=13.547 Å. Evaluation of the systematic absences in the XRD pattern indicated the following most possible space groups: $P6_3cm$, $P\text{-}6c2$, $P6_3/mcm$, $P31c$, and $P\text{-}3c1$. After activation, the symmetry of the UTSA-20 structure remains unchanged. We then solved the crystal structure using the direct method, and space group was identified as $P6_3/mcm$. Finally, Rietveld refinement was performed on the XRD pattern collected on the activated sample, using the GSAS package. Refinement on the lattice parameters, background, peak profile, as well as the atomic positions of Cu, C and O with constraints applied on C—C and C—O bonds lengths yields the agreement factors of $R_{wp}$=0.0811 and $R_p$=0.0644, which strongly supports the validity of our structure solution. Note that the quality and insensitivity of laboratory XRD data do not allow accurate location of H atoms, and thus the positions of H were estimated from the geometry and the common bond length of C—H. The refined lattice parameters are $\alpha$=22.286(1) Å and c=12.816(1) Å. CCDC-795055 (UTSA-20) contains the supplementary crystallographic data for this paper. These data can be obtained free of charge from The Cambridge Crystallographic Data Centre via www.ccdc.cam.ac.uk/conts/retrieving.html (or from the Cambridge Crystallographic Data Centre, 12 Union Road, Cambridge CB21EZ, UK; fax: (+44)1223-336-033; or deposit@ccdc.cam.ac.uk).

The following articles are incorporated by reference as if fully set forth herein:

[1] A. U. Czaja, N. Trukhan, U. Müller, *Chem. Soc. Rev.* 2009, 38, 1284.

[2] http://www.ecofuel-world-tour.com

[3] O. M. Yaghi, M. O'Keeffe, N. W. Ockwig, H. K. Chae, M. Eddaoudi, J. Kim, *Nature* 2003, 423, 705; S. Kitagawa, R. Kitaura, S. Noro, *Angew. Chem. Int. Ed.* 2004, 43, 2334; M. Dinca, J. R. Long, *Angew. Chem. Int. Ed.* 2008, 47, 6766; R. E. Morris, P. S. Wheatley, *Angew. Chem. Int. Ed.* 2008, 47, 4966; J. M. Thomas, *Topics in Catalysis,* 2008, 50, 98; T. Dueren, Y.-S. Bae, R. Q. Snurr, *Chem. Soc. Rev.* 2009, 38, 1237; L. Ma, C. Abney, W. Lin, *Chem. Soc. Rev.* 2009, 38, 1248; G. Férey, C. Serre, *Chem. Soc. Rev.* 2009, 38, 1380; B. Chen, S.-C. Xiang, G.-D. Qian, *Acc. Chem. Res.* 2010, 43, 1115.

[4] H. Furukawa, N. Ko, Y. B. Go, N. Aratani, S. B. Choi, E. Choi, A. O. Yazaydin, R. Q. Snurr, M. O'Keeffe, J. Kim, O. M. Yaghi, *Science,* 2010, 239, 424.

[5] K. Farha, A. O. Yazaydin, I. Eryazici, C. D. Malliakas, B. G. Hauser, M. G. Kanatzidis, S. T. Nguyen, R. Q. Snurr and J. T. Hupp, *Nat. Chem.* 2010, 944.

[6] F. Nouar, J. F. Eubank, T. Bousquet, L. Wojtas, M. J. Zawarotko, M. Eddaoudi, *J. Am. Chem. Soc.* 2008, 130, 1833.

[7] D. Yuan, D. Zhao, D. Sun and H.-C. Zhou, *Angew. Chem. Int. Ed.* 2010, 49, 5357.

[8] Y. Yan, I. Telepeni, S. Yang, X. Lin, W. Kockelmann, A. Dailly, A. J. Blake, W. Lewis, G. S. Walker, D. R. Allan, S. A. Barnett, N. R. Champness and M. Schroder *J. Am. Chem. Soc.* 2010, 132, 4092.

[9] J. Zhang, T. Wu, S.-M. Chen, P. Feng, X. Bu, *Angew. Chem. Int. Ed.* 2009, 48, 3486.

[10] Y.-B. Zhang, W.-X. Zhang, F.-Y. Feng, J.-P. Zhang, X.-M. Chen, *Angew. Chem. Int. Ed.* 2009, 48, 5287.

[11] A. J. Lan, K. H. Li, H. H. Wu, D. H. Olson, T. J. Emge, W. Ki, M. C. Hong and J. Li, *Angew. Chem. Int. Ed.,* 2009, 48, 2334.

[12] M. O'Keeffe, M. A. Peskov. S. J. Ramsden, O. M. Yaghi, *Accounts Chem. Res.* 2008, 41, 1782.

[13] Z. Chen, S.-C. Xiang, T. Liao, Y. Yang, Y.-S. Chen, Y. Zhou, D. Zhao and B. Chen, *Crystal Growth & Design,* 2010, 10, 2775.

[14] Burchell, T; Rogers, M. *SAE Tech. Pap. Ser.* 2000, 2000-01-2205.

[15] CHN elemental analysis (%) for UTSA-20 ($C_{48}H_{65}N_6O_{23.5}Cu_3$): calcd: C, 44.60; H, 5.07; N, 6.50%; found: C, 44.36; H, 4.69; N: 6.39%.

[16] T. Dueren, F. Millange, G. Ferey, K. S. Walton, R. Q. Snurr, *J. Phys. Chem. C,* 2007, 111, 15350.

[17] S.-C. Xiang, W. Zhou, J. M. Gallegos, Y. Liu and B. Chen, *J. Am. Chem. Soc.,* 2009, 131, 12415; S.-C. Xiang, W. Zhou, Z. Zhang, Y. Liu, B. Chen, *Angew. Chem. Int. Ed.,* 2010, 49, 4615.

[18] S.-I. Noro, S. Kitagawa, M. Kondo, K. Seki, *Angew. Chem. Int. Ed.* 2000, 39, 2081.

[19] M. Kondo, M. Shimamura, S.-I. Noro, S. Minakoshi, A. Asami, K. Seki, S. Kitagawa, *Chem. Mater.* 2000, 12, 1288.

[20] M. Eddaoudi, J. Kim, N. Rosi, D. Vodak, J. Wachter, M. O'Keeffe, O. M. Yaghi, *Science,* 2002, 295, 469.

[21] S. Ma, D. Sun, J. M. Simmons, C. D. Collier, D. Yuan, H.-C. Zhou, *J. Am. Chem. Soc.* 2008, 130, 1012.

[22] P. L. Llewellyn, S. Bourrelly, C. Serre, A. Vimont, M. Daturi, L. Hamon, G. D. Weireld, J.-S. Chang, D.-Y. Hong, Y. K. Hwang, S. H. Jhung and G. Ferey, *Langmuir* 2008, 24, 7245.

[23] X.-S. Wang, S. Ma, K. Rauch, J. M. Simmons, D. Yuan, X.-S. Wang, T. Yildirim, W. C. Cole, J. J. Lopez, A. De Meijere, H.-C. Zhou, *Chem. Mater.* 2008, 20, 3145.

[24] H. Wu, W. Zhou, T. Yildirim, *J. Phys. Chem. C* 2009, 113, 3029.

[25] H. Kim, D. G. Samsonenko, S. Das, G.-H. Kim, H.-S. Lee, D. N. Dybtsev, E. A. Berdonosova and K. Kim, *Chem. Asian J.* 2009, 4, 886.

[26] H. Wu, W. Zhou, T. Yildirim, *J. Am. Chem. Soc.* 2009, 131, 4995.

[27] H. Wu, J. M. Simmons, Y. Liu, C. M. Brown, X.-S. Wang, S. Ma, V. K. Peterson, P. D. Southon, C. J. Kepert, H.-C. Zhou, T. Yildirim and W. Zhou, *Chem. Eur. J.* 2010, 16, 5205.

[28] The claim of 220 $cm^3/cm^3$ for PCN-14 was carried out at a lower temperature of 290 K. The expected volumetric methane storage capacity is expected to be lower at 300 K.

[29] A. R. Millward and O. M. Yaghi *J. Am. Chem. Soc.,* 2005, 127, 17998.

[30] W. Zhou, *Chem. Rec.* 2010, 10, 200.

[31] D. Frenkel and B. Smit, *Understanding Molecular Simulation: From Algorithms to Applications.* San Diego: Academic Press, 2002.

[32] P. Giannozzi, S. Baroni, et al. *J. Phys.: Condens. Matter* 2009, 21, 395502.

[33] V. Barone, M. Casarin, D. Forcer, M. Pavone, M. Sambi, A. Vittadini, *J. Comput. Chem.* 2009, 30, 934.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A metal-organic framework comprising a 3,3',3",5,5',5"-benzene-1,3,5-triyl-hexabenzoate or a derivative thereof and copper, made by the method comprising:
    reacting 3,3',3",5,5',5"-benzene-1,3,5-triyl-hexabenzoic acid and a copper salt and an acid in a polar solvent;
    allowing the reaction to run at a temperature of at least 50° C. for at least one day; and
    separating the metal-organic framework from the polar solvent.

2. The metal-organic framework of claim 1, comprising a linker channel site comprising at least two organic linkers.

3. A metal-organic framework, comprising a 3,3',3",5,5', 5"-benzene-1,3,5-triyl-hexabenzoate or a derivative thereof and copper, wherein the 3,3',3",5,5',5"-benzene-1,3,5-triyl-hexabenzoate or derivative thereof and the copper coordinate to one another to form a microporous framework comprising open copper sites and linker channel sites.

4. The metal-organic framework of claim 3, wherein the metal-organic framework is configured to store methane.

5. The metal-organic framework of claim 3, wherein the metal-organic framework comprises a plurality of linker channel sites configured to bind to a gas with at least two organic linkers forming the metal-organic framework.

* * * * *